United States Patent [19]

Wan

[11] Patent Number: 5,451,661
[45] Date of Patent: Sep. 19, 1995

US005451661A

[54] PROCESS FOR MAKING LIPID CONJUGATES

[75] Inventor: Barbara Y. Wan, Tewksbury, Mass.

[73] Assignee: Genzyme Corporation, Cambridge, Mass.

[21] Appl. No.: 147,270

[22] Filed: Nov. 5, 1993

Related U.S. Application Data

[63] Continuation-in-part of Ser. No. 972,361, Nov. 5, 1992, Pat. No. 5,329,029.

[51] Int. Cl.$^6$ .................. A61K 37/02; C07K 1/00; G01N 33/92; C08H 1/00
[52] U.S. Cl. .................. 530/345; 530/402; 530/409; 530/410; 436/71; 436/142; 424/417; 424/418; 424/420
[58] Field of Search .................. 424/417, 418, 420; 436/71, 142, 139, 141; 514/9, 43; 530/402, 345, 410, 409; 554/48, 49, 80, 81, 82, 83

[56] References Cited

U.S. PATENT DOCUMENTS 5,171,678 12/1992 Behr et al. .................. 435/172.3

OTHER PUBLICATIONS

Loughrey, H. et al. (1990) "Optimized procedures for the coupling of proteins to liposomes" *Journal of Immunological Methods*, 132:25–35.

Afzelius, P. et al. (1988) "Covalent modification of serum transferrin with phospholipid and incorporation into liposomal membranes" *Biochima et Biophysica Acta*, 979:231–238.

Hutchinson F. et al. (1988) "Lectin–mediated targeting of liposomes to a model surface: An ELISA method" *FEBS Letters*, 234 (2):493–496.

Heath, Timothy D. (1987) "Covalent Attachment of Proteins to Liposomes" *Methods in Enzymology*, 149(10):111–119.

Heath, T. D. et al. (1986) "The Development and Application of Protein-Liposome Conjugation Techniques" *Chemistry and Physica of Lipids*, 40:347–358.

Fogler, W. et al. (1985) "Distribution and Fate of Free and Liposome-Encapsulated [$^3$H] Nor–Muramyl Dipeptide and [$^3$] Muramyl Tripeptide Phosphatidylethanolamine in Mice" *The Journal of Immunology*, 1135(2):1372–1377.

Birkhahn, R. et al. (1978) "Intravenous feeding of the rat with short chain fatty acid esters II. Monoacetoacetin$^{1-3}$" *The American Journal of Clinical Nutrition*, 31:436–441.

Birkhahn R. et al. (1978) "Monoglyceryl Acetoacetate: A Ketone Body–Carbohydrate Substrate for Parental Feeding of the Rat$^{1-3}$" *J. Nutr.*, 109:1168–1174.

Kato, Tetsuzo (1973) "Recent Synthetic Studies Using Diketene" *Accounts of Chemical Research*, 7:265–271.

Ukawa et al. "Synthesis & Antitumor Activity of New Alkylphospholipids Containing Modifications of the Phosphocholine Moiety" *Chem PharmBull* 37(s):1249–1255 1989.

Scandurra et al. "Functional Residues at the Active Site of Horse Liver Phosphopantothenoylcysteine Decarboxylase" *FEBS letters* 231(1):192–196 1988.

*Primary Examiner*—Michael G. Wityshyn
*Assistant Examiner*—Nancy J. Degen
*Attorney, Agent, or Firm*—William G. Gosz

[57] ABSTRACT

A process is described for generating conjugates of lipids and biologically active agents to produce compositions having therapeutic utility, such as drug delivery vehicles. The process involves mixing the reactive lipid with an appropriate amount of diketene to form an acetoacetylated lipid which is then isolated, dissolved in a suitable medium, and mixed with a nucleophilic-containing biologically active agent to form a biologically active agent-lipid conjugate. Alternatively, the acetoacetylated lipid can be mixed with a polyamine to form a cationic lipid.

9 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Pro  Phe  Gly  Lys
    1

PROCESS FOR MAKING LIPID CONJUGATES

RELATED APPLICATIONS

The application is a continuation-in-part of U.S. Ser. No. 07/972,361, filed Nov. 5, 1992, now U.S. Pat. No. 5,329,029, the contents of which are hereby incorporated by reference.

BACKGROUND OF THE INVENTION

Living cells are principally comprised of proteins, carbohydrates and lipids. The plasma membrane enclosing cells and in fact all biological membranes are assemblies of lipid and protein molecules held together by noncovalent interactions. The three major types of lipids in cell membranes are phospholipids (the most abundant), cholesterol and glycolipids. All three are amphipathic, that is they have a hydrophilic ("water-loving" or polar) end and a hydrophobic ("water-hating" or non-polar) end.

When amphipathic molecules are surrounded on all sides by an aqueous environment, they tend to aggregate so as to bury their hydrophobic tails and leave their hydrophilic heads exposed to water. In so doing they can form any of the following structures: 1.) spherical micelles, with the tails inward, 2.) biomolecular sheets, or 3.) bilayers, with the hydrophobic tails sandwiched between the hydrophilic head group.

Most phospholipds and glycolipids spontaneously form bilayers in aqueous environments. Therefore, the formation of the lipid part of biological membranes is a self-assembly process. Moreover, such lipid bilayers tend to close on themselves to formed sealed compartments. For the same reason that lipid bilayers self-assemble, they self-seal when torn.

Although the lipid bilayer comprising a cell's plasma membrane is fluid, it is relatively impermeable and, therefore, serves as an effective barrier to the entry into the cytoplasm of a cell. This protective function is served by other biological membranes including mucous membranes (e.g. gastric mucosa and, nasal mucosa) and even skin.

However, for therapeutic purposes, it would be useful to get certain therapeutic agents through biological membranes. Liposomes are under investigation as vehicles for delivering therapeutic agents through biological membranes. Liposomes are spherical lipid structures that can be prepared in a manner that encapsulates water soluble biologically active molecules in the aqueous interior. When administered in vivo, liposomes fuse with biological membranes and thereby deliver the biologically active molecule contained within.

However, it has been found that liposomes injected into the body do not always deliver at the intended site and instead accumulate in the liver and spleen; and at sites of inflammation (Ostro, M. J. and P. R. Cullis, Am, J. Hosp. Pharm 46; 1576–1587 (1989)). Functionalized liposomes are being actively investigated as vehicles for targeted drug delivery. Galactosylated phospholipids, for example, have been incorporated in liposomes and used to deliver the liposomes specifically to asialoglycoprotein receptors of the hepatic system (Haensler, J. and F. Schuber, Glycoconjugate J. 1991,8, pp116–124). Immunoliposomes, constructed by covalent conjugation of antibodies to the phospholipid moieties on the liposomal surface, have also shown promise in targeting liposomes to specific cell tissues (Nassander, U. K., P. A. Steerenber, H. Poppe, G. Storm, L. G. Poels, W. H. De Jong, D. J. A. Crommelin, Canc. Res. 1992, 52, pp646–653, and Pinnaduwage, P. and L. Huang, Biochemistry 1992, 31, pp2850–2855).

In addition to targeting, the size of the liposomes have been reduced to improve their targeting and transfer through biological membranes. Straight chain lipid molecules have shown to be effective for delivering small peptides. For example, the phospholipid phosphatidyl ethanolamine conjugated to muramyl tripeptide to form (MTP-PE) has been found to be active in vivo and was found present in various organs 24 hours after injection, whereas the parent peptide was found to be excreted out of the body 60 minutes after injection (Fogler, W. E., R. Wade, D. E. Brundish, I. J. Fidler, J. Immunol. 1985, 135, pp1372–1377, and Phillips, N. C., J. Rioux, M. -S.Tsao, Hepatology 1988, 8, pp 1046–1050). These results suggest that the absorption of a peptide is enhanced by conjugation to a lipophilic moiety. Other agents that have been coupled to phospholipids include acyclovir (Welch, C. J., A. Lamson, A. C. Ericson, B. Oberg, R. Datema, J. Chattopadhyaya, Acta Chem. Scand. 1985, B39, pp47–54), ganglioside $G_{M1}$ (Pacuszka, T., R. M. Bradley, P. H. Fishman, Biochemistry 30, pp2563–2570), oligosaccharides (Childs, R. A., K. Ddckamer, T. Kawasaki, S. Thiel, T. Mizuochi, T. Feizi, Blochem. J. 1989, 262, pp131–138), serum transferrin (Azelius, P., E. J. F. Demant, G. H. Hansen, P. B. Jensen, Biochim. Biophys. Acta 1989, 979, pp231–238), biotin, and fluorescent reagents.

Various methods have been described for derivatizing phospholipids to facilitate their conjugation with other molecules or moleties (for review, see Heath, T. D. and F. J. Martin, Chemistry and Physics of Lipids 1986, 40, pp347–358). However, each of these methods suffers from various difficulties in practical application. For example, one method comprises glutaraldehyde activation of phosphatidylethanolamine and ultimate conjugation to amines by reductive amination. The problem of dimerization both between the phospholipids and between proteins has made this method less than ideal. An alternative method comprises amide formation between phosphatidylethanolamine and the carboxyl terminus of a peptide or protein. However, this method suffers from low yields and formation of by-products.

In yet another approach, the phospholipid and the protein are first activated and then reacted to form the conjugate. For example, Hutchinson et. al. describe a method in which a phosphatidylethanol-amine is activated with N-succinimidyl-S-acetyl-thioacetate (SATA) and treated with a hydroxylamine to yield a phospholipid-thiol derivative. The protein of interest is also activated with maleimide and then treated with the phospholipid derivative to form a stable conjugate via a thioether (Hutchinson et. al., FEBS Lett. 1986, 234, pp493–6). In a variation of this protocol, the phosphatidylethanolamine is activated with a maleimido moiety and the lysine residue of a protein is activated with a protected thiol (Loughrey, H. C. et. al., J. Immun. Methods 1990, 132, pp25–35). In practice, protocols employing these approaches are cumbersome to perform and the cost of the derivatizing agent is prohibitively expensive for scales above multigram quantities.

Phospholipid conjugates have also been formed by functionalizing phosphatidylethanolamine using a crosslinking reagent (e.g. dithiobis(succinimidyl propionate)) and reacting this intermediate with a lysine-containing protein so that the succinimidyl moiety is displaced by the amino group of the lysine residue (Afzelius, P., *Blochem. Biophys. Acta* 1989, 979, pp231–8). However, crosslinking reagents are not economically feasible for producing phospholipid conjugates, particularly on a large scale. In yet another method, phosphatidylethanolamine may be coupled to glycosylated proteins via the protein carbohydrate chain. For example, glycans can be oxidized with sodium periodate to give reactive aldehydes which can then be coupled to phosphatidylethanolamine via reductive amination with sodium cyanoborohyddde (Heath, T. et. al., *Biochim. Biophys. Acta* 1980, 599:42). This method is limited in its application only to glycoproteins and is often associated with low yields and byproduct formation.

None of the heretofore described methods offer a simple, generally applicable, efficient and economical (i.e. practical) means for generating phospholipid or other lipid conjugates.

SUMMARY OF THE INVENTION

In general, the invention features a practical, easily performed process for conjugating biologically active agents to certain reactive lipids (i.e. nucleophile—containing lipids such as lipoamines and lipoalcohols). The process involves mixing an appropriate concentration of the reactive lipid with an appropriate amount of diketene at a suitable temperature and pH and for an appropriate period of time to form an acetoacetylated lipid which can then be isolated, dissolved in a suitable medium, and mixed with a nucleophilic-containing biologically active agent to form a biologically active agent-lipid conjugate. Alternatively, the acetoacetylated lipid can be mixed with a polyamine to form a cationic lipid.

Preferred reactive lipids for use in the subject invention include phospholipids, glycolipids, polyisoprenoids, ether lipids or steroids having at least one nucleophilic alcohol or amine moiety. Especially preferred starting lipids are phosphatidylalkanolamines.

Biologically active agent-lipid conjugates made by the process of the subject invention are useful, for example, for delivering biologically active agents through biological membranes and to cells, are useful as adjuvants and also for studying membrane biophysics. Cationic lipids prepared according to the method herein are also useful for drug delivery.

DETAILED DESCRIPTION

As used herein, the following words and phrases shall have the following meaning:

Definitions

"biologically active agent"—shall mean a peptide, protein, nucleic acid (e.g. DNA or RNA), carbohydrate or other compound (e.g. drug)

"nucleophile-containing biologically active agent"—shall mean a biologically active agent having an amino (—$NH_2$) or hydrazino (—NH—$NH_2$) moiety. For example an amino moiety can be present at the amino terminus of a protein or peptide or may be present if the protein or peptide includes a lysine or ornithine residue.

"reactive lipid"—shall mean a nucleophile-containing substance that is soluble in an organic solvent. Examples of reactive lipids include lipoamines (i.e. lipids containing an amine moiety —NH) and lipoalcohols (i.e. lipids containing an alcohol moiety —OH). Reactive lipids may be for example phospholipids (i.e. composed of a glycerol backbone acylated with fatty acids at the $C_1$, and $C_2$ positions and phosphorylated at the remaining terminus); ether lipids (i.e. lipids with an alkyl (or alkenyl) group connected to the hydroxyl function of glycerol (e.g. platelet activating factor)); glycolipids (i.e. lipids composed of a hydrophilic region containing 2 long hydrocarbons tails and a polar region which contains 1 or more sugar residues); polyisoprenoids (i.e. lipids composed of repeating isoprene units); or steroids (i.e. lipids composed of isoprene units in a ring structure (e.g. cholesterol and testosterone)).

Suitable reactive lipids as starting materials for the processes disclosed herein are of the general formula:

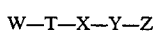

Where:

W is a long alkyl or alkenyl fatty acid chain, or a long alkyl or alkenyl chain, or asteroid with an amido or ester linkage,or a radical of general formula:

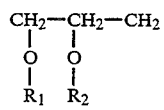

wherein $R_1$, $R_2$ independently represent alkyl, substituted alkyl, alkenyl, substituted alkenyl, alknyl, substituted alknyl, aryl, substituted aryl, arylalkyl, substituted arylalkyl; or $C(O)R_3$ where $R_3$ represents alkyl, substituted alkyl, alkenyl, substituted alkenyl, alknyl, substituted alknyl, aryl, substituted aryl, arylalkyl, substituted arylalkyl;

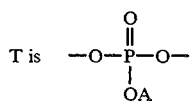

wherein A is a cationic moiety including H+, alkali metal ions, alkali earth metal ions, ammonium ion, and ammonium ions substituted with low alkyl groups; or —O—; or is absent;

X is alkyl, alkenyl, arylalkyl, substituted alkyl, substituted arylalkyl, substituted alkenyl, or is absent;

Y is an alkyl chain optionally substituted with amide, ester, amine, and ether linkages. One example may be a polyamine with an amide linkage such as

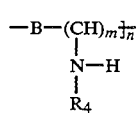

wherein n=1 to 5; m=2 to 6; $R_4$ is H, or a blocking group such as carbamates or amides; B is

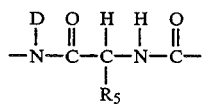

wherein $R_5$ is H, or an alkyl radical containing 1 to 4 carbon atoms optionally substituted with a phenyl radical, D is W—T—X as defined above, or is absent.

Another example of Y may be a radical of general formula

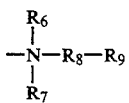

wherein $R_6$, $R_7$ independently represent H, or $C_1$ to $C_{24}$ alkyl or alkenyl groups; $R_8$ is $C_1$ to $C_{24}$ straight or branched alkyl chain; $R_9$ is —O—C(O)—(CH$_2$)$_p$—, or —O-aminocarboxylic acid which is alkyl, aryl,or arylalkyl; or —O—C(O)—(CH$_2$)$_p$—NH— linked to the said aminocarboxylic acid where p is 1 to 18, or is absent; and Z is —OH, or NH($R_{10}$) wherein $R_{10}$ represents H, alkyl, and aryl;

Phospholipids, which are the primary components of many biological membranes, are preferred starting materials for use in the disclosed process. Especially preferred are phosphatidylalkanolamines of the general formula:

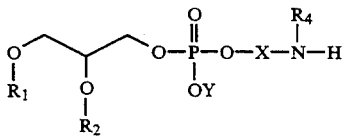

wherein $R_1$, $R_2$ independently represent alkyl, alkenyl, alkynyl, arylalkyl or C(O)$R_3$, wherein $R_3$ represents alkyl, alkenyl, alkynyl, aryl, and arylalkyl $R_4$ represents H, alkyl, aryl X represents alkyl, alkenyl, arylalkyl; and Y represents a cationic moiety including H$^+$, alkaline metal ions, alkali earth metal ions, ammonium ion, and substituted ammonium ions.

the alkyl, alkenyl, aryl, arylalkyl and alkynyl may optionally be substituted.

"diketene"—shall mean diketene itself

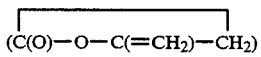

having the formula:

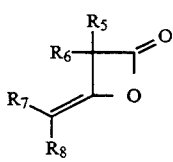

Wherein $R_5$, $R_6$, $R_7$, and $R_8$ represent H or a lower alkyl.

"acetoacetylated lipid"—shall mean a product obtained from reacting a reactive lipid with diketene and shall have the following general formula:

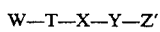

W is a long alkyl or alkenyl fatty acid chain, or a long alkyl or alkenyl chain, or asteroid with an amido or ester linkage,or a radical of general formula:

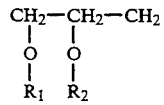

wherein $R_1$, $R_2$ independently represent alkyl, substituted alkyl, alkenyl, substituted alkenyl, alknyl, substituted alknyl, aryl, substituted aryl, arylalkyl, substituted arylalkyl; or C(O)$R_3$ where $R_3$ represents alkyl, substituted alkyl, alkenyl, substituted alkenyl, alknyl, substituted alknyl, aryl, substituted aryl, arylalkyl, substituted arylalkyl;

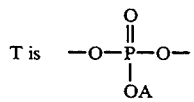

wherein A is a cationic moiety including H+, alkali metal ions, alkali earth metal ions, ammonium ion, and ammonium ions substituted with low alkyl groups, or —O—, or is absent;

X is alkyl, alkenyl, arylalkyl, substituted alkyl, substituted arylalkyl, substituted alkenyl, or is absent;

Y is an alkyl chain optionally substituted with amide, ester, amine, and ether linkages. One example may be a polyamine with an amide linkage such as

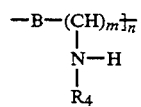

wherein n=1 to 5; m=2 to 6; $R_4$ is H, or a blocking group such as carbamates or amides; B is

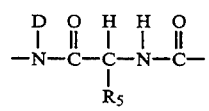

wherein $R_5$ is H, or an alkyl radical containing 1 to 4 carbon atoms optionally substituted with a phenyl radical, D is W—T—X as defined above, or is absent.

Another example of Y may be a radical of general formula

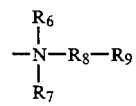

wherein $R_6$, $R_7$ independently represent H, or $C_1$ to $C_{24}$ alkyl or alkenyl groups; $R_8$ is $C_1$ to $C_{24}$ straight or branched alkyl chain; $R_9$ is —O—C(O)—(CH$_2$)$_p$—, or —O-aminocarboxylic acid which is alkyl, aryl, or arylalkyl; or —O—C(O)—(CH$_2$)$_p$—NH— linked to the said aminocarboxylic acid where p is 1 to 18, or is absent;

Z' is

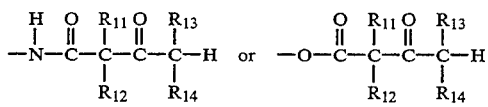

Phosphatidylalkanolamine reacted with diketene yield N-substituted phosphatidylalkanolamines having the general formula:

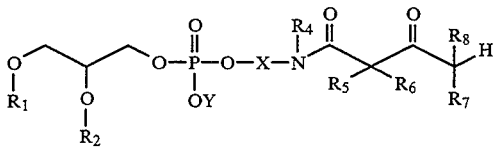

wherein $R_1$, $R_2$ independently represent alkyl, alkyl, alkenyl, alkynyl, arylalkyl or $C(O)R_3$, wherein $R_3$ represents alkyl, alkenyl, alkynyl, aryl, and arylalkyl $R_4$ represents H, alkyl, aryl $R_5R_6$ independently represent H, alkyl $R_7R_8$ independently represent H, alkyl X represents alkyl, alkenyl, arylalkyl; and Y represents a cationic moiety including H+, alkali metal ions alkali earth metal ions, ammonium ion, and substituted ammonium ions.

the alkyl, alkenyl, aryl, arylalkyl and alkynyl may optionally be substituted.

"amine" shall mean a compound containing an NH or $NH_2$ unit

"polyamine"—a compound containing three or more NH or $NH_2$ units.

"substituted" shall mean functionally modified with a hydroxy group (e.g. ethers and esters); amino group (e.g. amides); halogen atoms; trifluromethyl group; or carboxyl group (e.g. esters and amides).

In general, the process of the subject invention comprises mixing a reactive lipid with a diketene, thereby producing an acetoacetylated lipid and then mixing acetoacetylated lipid with a suitable biologically active agent or a polyamine to generate a conjugate. For use in the subject invention, a starting reactive lipid may be synthetic, semi-synthetic or isolated from natural sources. Naturally occurring lipids, for example, can be extracted from bovine brain, sheep brain, bovine liver, porcine liver, soybean, egg yolk or cell extracts from E. coli. Synthetic lipids can be obtained, for example, from vadous commercial vendors.

According to one method of the invention, an acetoacetylated lipid is produced from a starting reactive lipid upon reaction with diketene. Preferably the reaction is carried out in an organic solvent mixture, (e.g. a mixture of methanol and chloroform or dichloromethane). Solvent mixtures containing primary and secondary amines should be avoided as the amines will compete with the reactive lipid for reaction with diketene. Preferably the concentration of the reactive lipid used is in the range of from about 0.001 to 0.1M. A concentration of 0.01–0.05M is especially preferred. Preferably the pH of the solution is kept in the range of 3–8. However a pH in the range of 4–7 is especially preferred. The reaction should be run at a temperature at which the reactive lipid is completely soluble in the particular organic solvent. For example, temperatures in the range of 10° C. to 50° C. are generally useful, although this range can vary depending on the solvent system and the overall nature of the reactive lipid. Lipoalcohols may have to be heated to temperatures greater than 100° C. in order to react.

An excess of diketene can be added to the reactive lipid. Preferably the ratio of diketene to reactive lipid is in the range of from about 0.9:1 to 100:1, with a ratio of greater than 15:1 being particularly preferred. A low ratio of diketene to reactive lipid or impure diketene may result in partial reactions and low yields.

The reaction mixture can be stirred at the aforementioned temperature until all the reactive lipid has reacted. This typically requires 1 to 48 hours, after which the acetoacetylated lipid derivative may be isolated using standard methods known to those skilled in the art. For example, the reaction mixture can be concentrated to less than half of its original volume and the product precipitated by acetone. The precipitate, usually a white powder, may be collected either by filtration or centrifugation. More product may be obtained by further evaporation of the mother liquor and precipitation by acetone. Other isolation methods include column chromatography and crystallization. The purified acetoacetylated lipid may be analyzed for example using nuclear magnetic resonance spectroscopy (NMR), infrared spectroscopy (IR), thin layer chromatography (tlc) or high pressure liquid chromatography (HPLC).

The acetoacetylated lipids of the subject invention can be contacted with a nucleophile containing biologically active agent to form a biologically active agent—lipid conjugate. Alternatively, an acetoacetylated lipid may be conjugated with an amine or polyamine to produce a "cationic lipid", (i.e. a lipid having a net positive charge).

For example, an acetoacetylated lipid may be conjugated to a nucleophile—containing biologically active agents via a pendant amino group (e.g. an amino terminus or a lysine or ornithine residue of a peptide or protein) or via a hydrazino group. Primary and secondary amino groups are preferred, with primary amino groups being especially preferred because reactions can proceed without steric hindrance.

Nucleophile containing biologically active agents, amines or polyamines (hereinafter referred to as amino compounds) to be conjugated with an acetoacetylated lipid as described herein may, for example, be synthesized chemically, isolated from natural sources, or obtained via genetic engineering technology. Examples of biologically active agents to be conjugated with an acetoacetylated lipid can include, but are not limited to, thyroid stimulating hormone, p-glucocerebrosidase, cystic fibrosis transmembrane regulator, prolactin, comosain, ananain, α-galactosidase, thyrotropin releasing hormone, insulin, vasopressin, calcitonin, oxytocin, prolactin, amylin, luteinizing hormone releasing hormone peptide portions of these proteins and nucleic acids coding therefore. Polyamines for use in the instant process can include lipopolyamines (e.g. as described in U.S. Pat. No. 5,171,678 "Lipopolyamines, Their Preparation and Use" by Behr and Loeffler).

In general, conjugation of an acetoacetylated lipid with an a biologically active agent containing an amino (NH) and/or hydrazino ($NH-NH_2$) moiety can be accomplished by mixing the two compounds in a suitable medium to form an imine intermediate, which if necessary may be reduced to yield a stable amino linkage.

Preferably, prior to being reacted with an amino or hydrazino compound, an acetoacetylated lipid is dissolved in an organic solvent. Chlorinated solvents or a mixture of chlorinated solvents and methanol are preferred. An acetoacetylated lipid may also be dissolved in an aqueous buffer which contains one or more detergents. Preferably the molarity of an acetoacetylated is in the range of from about 1 mM to 1.0M. However, a molarity in the range of 10 mM–100 mM especially preferred.

Prior to being reacted with an acetoacetylated lipid, an amine containing biologically active agent/or polyamine can be dissolved in either an organic or an aqueous medium. Examples of typical organic mediums include chloroform, dichloromethane, methanol, dimethylformamide or dimethylsulfoxide. An example of a typical aqueous medium is a mild buffer solution. However, buffers which contain primary and secondary amines should be avoided as they will compete with the amino group for reaction with the lipid.

The ratio of the acetoacetylated lipid to the amino compound may be 1:1 or any of the two reactants may be in excess. The mixture of acetoacetylated lipid, amino compound and the reducing agent can be allowed to react at a temperature in the range of about 0° C. to 60° C. for a period of time ranging from about 4 to 60 hrs.

Preferably the pH of the resulting solution is kept in the range of about 2 to 9. However, a pH value in the range of 4 to 6 is especially preferred, as it favors the formation and the subsequent reduction of the imine intermediate.

The imine moiety formed between the acetoacetylated lipid and the amino compound may be reduced further to give a stable amino linkage. Sodium cyanoborohydride is a preferred reducing agents because it is specific for the reduction of the imine moiety. The molar ratio of the reducing agent to the imine may vary in accordance with the particular reducing agent used. A preferred ratio of sodium cyanoborohydride to imine is 3 to 1 or higher.

The reductive amination product may be isolated from the mixture for example, by acetone precipitation or, by other standard methods such as silica gel chromatography or crystallization. The new lipid conjugate may then be characterized (e.g. using standard tlc, NMR or HPLC methods).

Utility

The instant claimed process provides an efficient, cost-effective means for generating lipid conjugates. For example, this process may be useful for conjugating a lipid to a biologically active agent. Such lipid-biologically active agent conjugates either "as are" or prepared as liposomes may function as "drug delivery vehicles" facilitating transport of the biologically active agent through mucus membranes and into the blood stream (e.g. for oral delivery of the biologically active agent) and/or through plasma membranes and into cells. (Shen et. al. Advanced Drug Delivery-Reviews 8:105 (1992)).

The process described herein may also be useful for conjugating lipids to biologically active agents which are recognized by cell surface proteins (e.g. receptors). Incorporation of these lipid conjugates into delivery vehicles (e.g. liposomes or microspheres) may be used to target cells having the particular surface protein. For example lipid-epidermal growth factor conjugates may be used to target cells having growth factor receptors.

Use of the subject process for conjugating polyamines to neutral or anionic lipids is useful for generating cationic lipids, which themselves ionically interact with nucleic acids forming a lipophilic complex which can be used e.g. for transfection of cells in vivo or in vitro. (See e.g. WO 91/16024 "Cationic Lipids for Intracellular Delivery of Biologically Active Molecules" by Felgner et. al.)

Lipid conjugates of peptides or carbohydrates produced by the method described herein may increase the immunogenicity of the parent peptide or carbohydrate and therefore be useful as an adjuvant.

Fluorescently labelled lipid-biological molecule conjugates can be prepared as membrane probes (e.g. to study membrane biophysics (Molecular Probes Inc. Catalogue).

The present invention will now be illustrated by the following examples, which are not intended and should not be construed as being limiting in any way.

Example 1: Synthesis of 1,2-distearoyl-sn-glycero-3-phospho-(N-acetoacetyl)-ethanolamine (N-acetoacetyl-distearoyl-phosphatidylethanolamine, N-acetoacetyl distearoyl phosphatidylethanolamine, N-acetoacetyl DSPE)

A solution of distearoyl-phosphatidylethanolamine (1.42 g, 1.64 mmol) (Genzyme Corporation, Cambridge, Mass.) in a 3:1 mixture of chloroform/methanol (60 mL total) was warmed to 50° C. until all of the phosphatidylethanolamine dissolved. To the resulting solution was added diketene (5 mL, 65 mmol). The solution was stirred at 40° C. for 6 h. Another batch of diketene (5 mL, 65 mmol) was added. The mixture was then stirred at 40° C. for an additional 16 h. Thin layer chromatography analysis of the reaction mixture on silica coated plate (65:35:5 chloroform/methanol/water, visualized by molybdenum blue reagent) showed that all starting phosphatidylethanolamine ($R_f$ value: 0.49) had reacted and that a new phospholipid derivative ($R_f$ value: 0.54) was formed. The reaction mixture was concentrated under reduced pressure to about one-third of the original volume by rotoevaporation and acetone (about 20 mL) was added to the mixture until a white precipitate formed. The heterogeneous mixture was allowed to stand for about 15 min. The precipitate was collected by centrifugation and washed with cold acetone (5 ml). The collected solid was then dried under high vacuum (560 mg, 36% yield). Additional product was obtained by evaporating the filtrate to about one-sixth of its original volume followed by precipitation with acetone (about 20 mL). The precipitate was collected as described above (650 mg, 42%).

NMR analysis of the product (3:1 CDCl$_3$/MeOH-d4) using a Varian VXR 400 MHz machine showed a downfield shift of the methylene group (—CH$_2$—NH) from 3.2 ppm to 3.4 ppm. The shift is consistent with an amide formed from a primary amine. Furthermore, the presence of a singlet at 2.3 ppm is also indicative of the methyl ketone in the N-acetoacetyl moiety. $^1$H NMR (CDCl$_3$): δ 5.25 (br. s, 1 H), 4.37 (dd, J=6, 12 Hz, 1 H), 4.10 (overlapping m and br. s, 5 H), 3.55 (br. s, 2 H), 3.50 (s, 2 H), 2.33 (dd, J=7 Hz, 4 H), 2.30 (s, 3 H), 1.80 (br. s, 4 H), 1.25 (br. s, 56 H), 0.9 (t, J=7 Hz, 6 H).

Example 2: Synthesis of 1,2-dimyristoyl-sn-glycero-3-phospho-(N-acetoacetyl)ethanolamine (Nacetoacetyl dimyristoyl phosphatidylethanolamine, N-acetoacetyl DMPE)

To a solution of dimyristoyl phosphatidylethanolamine (24 mg, 0.03 mmol) (Genzyme Corp., Cambridge, Mass.) in a 3:1 mixture of chloroform/methanol (4 mL) was added an excess of diketene (1 mL). The resulting homogeneous mixture was stirred at room temperature for 19 h. The reaction mixture was concentrated under reduced pressure to less than 1 mL and acetone (about 5 mL) was added to the concentrated reaction mixture. The white precipitate formed was collected by centrifugation as described in example 1 (13 mg, 50%). $^1$H NMR (3:1 CDCl$_3$/MeOH-d$_4$): δ5 5.17 (br. s, 1 H), 4.32 (br. d, J=11 Hz, 1 H), 4.05 (m, 3 H), 3.93 (m, 2 H), 3.89 (m, 2 H), 3.42 (br. t, J=8.4 Hz, 2 H), 2.25 (t, J=6 Hz, 4 H), 2.21 (s, 3 H), 1.53 (hr. s, 4 H), 1.25 (br.s), 0.83 (t, J=6 Hz, 6 H).

Example 3: Reductive amination of N-acetoacetyl distearoyl phosphatidylethanolamine with α-N-acetyl lysine methyl ester A solution of N-acetoacetyl distearoyl phosphatidylethanolamine (94 mg, 0.1 mmol), α-N-acetyl lysine ethyl ester (HCl salt, 127 mg, 0.5 mmol) (Sigma Chemical Co.), triethylamine (67 uL, 0.5 mmol), sodium cyanoborohydride (10 mg, 0.16 mmol) was stirred at room temperature for 68 hr. A yellow solution and a small amount of white solid was formed. The solid was removed from the reaction mixture by centrifugation and the resulting solution was evaporated to dryness to give a yellow gum. The yellow gum was triturated with 1:1 methanol/acetone (5 mL) and the white precipitate thus formed was collected by centrifugation (60 mg). The crude product was further purified on a silica gel column equilibrated with 1:1 chloroform/methanol to give a white solid (25 mg, 22% yield). $^1$H NMR(3:1 CDCl$_3$/MeOH-d$_4$) δ5.18 (br.s, 1 H), 4.38 (m, 1 H), 4.35 (dd, J=3, 12 Hz, 1 H), 4.10 (dd, J=5, 12 Hz, 1 H), 4.05 (m, 1 H), 3.9 (t, J=6 Hz, 2 H), 3.68 (s, 3 H), 3.45 (br. d, J=13 Hz, 2 H), 3.20 (m, 1 H), 2.87 (m, 1 H), 2.78 (m, 1 H), 2.42 (br. s, 2 H), 2.25 (overlapping t, J=7 Hz, 4 H), 1.95 (s, 3 H), 1.78 (m, 1 H), 1.62 (m, 3 H), 1.46 (br. s, 4 H), 1.38 (m, 2 H), 1.20 (br. s), 0.8 (overlapping t, J=7 Hz, 6 H). Thin layer chromatography analysis (65:35:5 chloroform/methanol/water): R$_f$ for N-acetoacetyl distearoyl phosphatidyl-ethanolamine 0.69, for product 0.78.

Example 4: Reductive Amination of N-acetoacetyl distearoyl phosphatidylethanolamine with Pro-Phe-Gly-Lys (SEQ ID NO: 1)

To a stirred solution of the tetrapeptide Pro-Phe-Gly-Lys (SEW ID NO: 1) (40 mg, 0.08 mmol) (Sigma Chemical Co.)in methanol (2 mL) was added a solution of N-acetoacetyl distearoyl phosphatidylethanolamine (74 mg, 0.08 mmol)in chloroform (2.5 mL). After stirring at ambient temperature for 30 min, a solution of sodium cyanoborohydride (17 mg, 0.27 mmol)in methanol (1 mL) was added. The resulting solution was allowed to stir at ambient temperature for 16 h, after which the reaction mixture was concentrated under reduced pressure to approximately 1 mL and the product was precipitated by addition of acetone (approximately 5 mL) at ambient temperature. The white precipitate was collected by centrifugation and was washed once with cold acetone (approximately 5 mL). The white precipitate was then redissolved in 1:1 chloroform/methanol and evaporated to dryness. Thin layer chromatography analysis (65:35:5 chloroform/methanol/water)showed disappearance of the N-acetoacetyl distearoyl phosphatidylethanolamine and concomittant formation of a new phospholipid derivative (R$_f$: N-acetoacetyl distearoyl phosphatidylethanolamine: 0.82, major product: 0.89). Reverse phase HPLC analysis of the reaction mixture using a YMC-A-301-3 column showed a major peak which was different from the tetrapeptide and N-acetoacetyl distearoyl phosphatidylethanolamine. HPLC analysis using a Phenomenex Sperisorb 3u Column (normal phase) on a Waters 600 E System equipped with a mass evaporative detector also showed one major peak (retention time: 24.98 min, area percent: 69.7). The HPLC data also confirmed that the new phospholipid derivative, as expected, was more hydrophobic than the tetrapeptide and, more hydrophilic than N-acetoacetyl distearoyl phosphatidylethanolamine.

To further characterize the product, an aliquot of the crude product was passed through a reverse phase column (YMC C$_{18}$ column, 10 mm×250 mm, 40:60:15:0.1 chloroform/methanol/water/trifluoroacetic acid) and the material under the major peak was isolated. The partially purifed product was then subjected to fatty acid and amino acid analyses. Results from these two analyses unequivocally indicated the existence of stearic acid, proline, phenylalanine, glycine and lysine in the same sample, thus confirming that the product isolated contained the amino acid constituents of Pro-Phe-Gly-Lys (SEQ ID NO: 1) and the stearic acid residues present in the N-acetoacetyl distearoyl phosphatidylethanolamine reagent. Selected $^1$H NMR data: δ5 7.19 (m, 2 H, aromatic H), 7.12 (m, 3 H, aromatic H), 5.13 (m, 1 H, (sn-2)CH), 4.43 (dd, J=4.4, 8.4 Hz, 1 H, part of (sn-1) CH$_2$), 4.07 (dd, J=6.8, 12 Hz, 2 H, (sn-3)CH$_2$), 2.21 (t, J=7.5 Hz, 4 H,—O—C(O)—CH$_2$—), 0.79 (t, J=7 Hz, 6 H, —O—(O)—C—(CH$_2$)$_{16}$—CH$_3$.

Example 5: Reductive amination of N-acetoacetyl distearoyl phosphatidylethanolamine with benzyl amine To a stirring solution of N-acetoacetyl distearoyl phosphatidylethanolamine (50 mg. 0,052 mmol) in chloroform (5 mL) was added benzyl amine (35 ul, 0.32 mmol) and sodium cyanoborohydride (10 mg, 0.16 mmol)in methanol (5 mL). The homogeneous solution was stirred at ambient temperature for 18 h. Thin layer chromatography analysis of the reaction mixture (65:35:5 chloroform/methanol/water) showed disappearance of N-acetoacetyl distearoyl phosphatidylethanolamine and appearance of two products (R$_f$ for N-acetoacetyl distearoyl phosphatidylethanolamine: 0.73, for major product: 0.77, for minor product: 0.76). The new phospholipid derivatives were isolated by acetone precipitation and centrifugation as described in example 1. Silica gel column chromatography was used to separate the two products. The minor product was eluted with 3:1 chloroform/methanol (7 mg, 13%) whereas the major product was eluted with 2:1 chloroform/methanol (30 mg, 56%). NMR analysis of the major product confirmed a 1:1 incorporation of benzyl amine into the phospholipid moiety. $^1$H NMR(3:1 CDCl$_3$/MeOH-d$_4$) δ7.4 (m, 5 H), 5.18 (br. s, 1 H), 4.32 (dd, J=3,12 Hz, 1 H), 4.11 (br. d, J =12 Hz, 1 H), 4.0 (m, 1 H), 3.88 (t, J=6 Hz, 2 H), 3.85 (m, 1 H), 3.41 (br. dd, J=4, 11 Hz, 2 H), 3.29 (m, 1 H), 3.22 (dd, J =4, 10 Hz, 1 H), 3.18 (dd, J=4, 10 Hz, 1 H), 2.50 (dd, J=8, 16 Hz, 1 H), 2.42 (dd, J=4, 16 Hz, 1 H), 2.22 (t, J=7 Hz, 2 H), 2.15 (t, J=7 Hz, 2 H), 1.58 (br.s, 4 H), 1.2 (br.s, 59 H),0.9 (overlapping t, J=7Hz, 6H).

The minor product was dissolved in a 1:1 mixture of chloroform/methanol (1 mL) and further subjected to sodium cyanoborohydride (2 mg) for 16 h at room temperature. Both NMR and tlc indicated that the new product formed from the second reduction was identical to the major product isolated previously, thus suggesting that the minor product was the imine intermediate between the N-acetoacetyl distearoyl phosphatidylethanolamine and benzyl amine.

Example 6: Reductive amination of N-acetoacetyl distearoyl phosphatidylethanolamine with Thr-Ser-Lys A solution of the tripeptide, Thr-Ser-Lys (4 mg, 8 umol) (Sigma Chemical Co.), N-acetoacetyl distearoyl phosphatidylethanolamine (11 mg, 12 umol), sodium cyanoborohydride (2 mg, 32 umol)in 1:1 chloroform/methanol (2 mL) was stirred at ambient temperature for 16 h, after which time the reaction mixture was concentrated under reduced pressure to about 0.5 mL, and acetone (about 3 mL) was added. The precipitate thus formed was collected by centrifugation (12 mg, quantitative). Thin layer chromatography on silica: $R_f$ for N-acetoacetyl distearoyl phosphatidylethanolamine 0.73, major product 0.30, minor product 0.45. HPLC analysis using a Phenomenex Sperisorb 3u Column (normal phase) on a Waters 600 E System showed that over 90% of the starting N-acetoacetyl distearoyl phosphatidylethanolamine had reacted to give four new products (retention times: 22.33 min, 22.35%; 23.08 min, 25.82%, 24.43 min, 37.81%, 25.55 min, 10.39%). These new products may represent peptide-phospholipids coupled at the amino terminus of the peptide, at the ε-amino group on the lysine residue, a diphospholipid-peptide coupled at both the amino terminus and the ε-amino group on the lysine, and imine intermediates formed between the N-acetoacetyl distearoyl phosphatidylethanolamine and the peptide.

Example 7: Reductive amination of N-acetoacetyl distearoyl phosphatidylethanolamine with Thr-Tyr-Ser To a suspension of the tripeptide, Thr-Tyr-Ser (9 mg, 0.024 mmol) (Sigma Chemical (Co.)in methanol (2 mL) was added a solution of N-acetoacetyl distearoyl phosphatidylethanolamine (25 mg, 0.026 mmol) in chloroform (2 mL). The mixture was stirred at room temperature for 1 h and sodium cyanoborohydride (10 mg) was added. The mixture was stirred at ambient temperature for 60 h and the solution phase was then separated from the solid phase by decantation. The solution was concentrated under reduced pressure to approximately 1 mL and the desired product mixture was isolated by acetone precipitation (approximately 5 mL). The white precipitate was collected by centrifugation and washed once with cold acetone (28 mg, 82%). Selected $^1$H NMR data: δ6.99 (dd, J=8 Hz, 2 H, aromatic H on Tyr), 6.66 (br. d, J=8 Hz, 2 H, aromatic H on Tyr), 5.18 (m, 1 H, (sn-2)CH), 2.23 (hr. t, J=7 Hz, 4 H, O—(O)—C—CH$_2$—), 1.52 (hr. s, 4 H, —O—(O)—C—CH$_2$—CH$_2$ —), 0.81 (t, J=7 Hz, 6 H, —(O)—C—(CH$_2$)$_{16}$CH$_3$).

Example 8: Reaction of N-acetoacetyl distearoyl phosphatidylethanolamine with dansyl hydrazide A round-bottom flask was charged with a solution of N-acetoacetyl distearoyl phosphatidylethanolamine (12 mg, 0.01 3 mmol) in chloroform (0.5 mL) and a solution of dansyl hydrazide (3 mg, 0.011 mmol) (Sigma Chemical Co.) in chloroform (0.9 mL). After stirring at 0° C. for 30 min, N-acetoacetyl distearoyl phosphatidylethanolamine was shown to have completely reacted and a new product, which showed fluorescence activity and was stained by molybdenum blue reagent, was formed. The reaction mixture was stirred at 0° C. for an additional 60 min and was then evaporated to dryness under reduced pressure. The resultant orange colored solid was purified on a silica gel column. The desired product was eluted from the column with 2:1 chloroform/methanol as a yellowish solid (11 mg, 81%). Thin layer chromatography analysis on silica (65:35:5 chloroform/methanol/water): $R_f$ for N-acetoacetyl distearoyl phosphatidylethanolamine 0.61, for product 0.72. NMR analysis of the product showed the absence of the methyl ketone moiety, and the incorporation of the dansyl moiety as evidenced by the presence of the aromatic protons between 7 and 8 ppm. Selected $^1$H NMR(400 MHz) δ:8.38 (m, 1 H), 8.30 (m, 1 H), 8.10 (m, 1 H), 7.40 (m, 2 H), 7.02 (m, 1 H), 5.05 (m, 1 H), 4.20 (br. d, J=12 Hz, 1 H), 4.0 (m, 2 H), 3.78 (m, 2 H), 3.70 (m, 2 H), 2.70 (s, 3 H), 2.68 (s, 3 H), 2.18 (br. t, J=7 Hz, 4 H), 1.50 (br. s, 4 H), 1.20 (br. s, 56 H), 0.78 (t, J=7 Hz, 6 H).

Example 9: Reductive Amination of N-acetoacetyl disteroyl phosphatidylethanolamine with (Arg$^8$)-vasopressin To a stirred solution of the (Arg$^8$)-vasopressin mg, 5 umole, Bachem Bioscience)in methanol (0.5 mL) was added a solution of N-acetoacetyl distearoyl phosphatidylethanolamine (7 mg, 8 umole) in chloroform (0.5 ml). After stirring at ambient temperature for 30 min, sodium cyanoborohydride (7 mg, 111 umole) was added. The resulting solution was allowed to stir at ambient temperature for 16 h. Reverse phase HPLC analysis of the reaction mixture using a YMC ODS-A column (4.6×100 mm, 3u, 120 Å, 400:600:150:1 chloroform/methanol/water/trifluoroacetic acid) showed a major peak which was different from (Arg$^8$)-vasopressin and N-acetoacetyl distearoyl phosphatidylethanolamine. This new product was isolated by preparative reverse phase HPLC (4 mg) and shown to be >99% pure. $^1$H NMR analysis (400 MHz) showed that the product was a 1:1 conjugate of the phospholipid and the peptide.

Equivalents

Those skilled in the art will recognize or be able to ascertain using no more than routine experimentation many equivalents to the specific embodiments of the invention described specifically herein. Such equivalents are intended to be encompassed in the scope of the following claims.

I claim:

1. A process for making a biologically active agent-lipid conjugate, comprising the steps of:
   a) mixing a reactive lipid in an organic solvent with a diketene thereby producing an acetoacetylated lipid;
   b) isolating the acetoacetylated lipid;
   c) dissolving the acetoacetylated lipid in a medium;
   d) mixing the dissolved acetoacetylated lipid with a nucleophile—containing biologically active agent thereby producing a biologically active agent—lipid conjugate; and
   e) isolating the biologically active agent—lipid conjugate.

2. The process of claim 1 wherein in step (a), the concentration of the reactive lipid is in the range of 0.001–0.1M and the mixing takes place at a temperature the range of 10° C.–50° C. and a pH in the range of 3–8; and in step (d), the concentration of acetoacetylated lipid is in the range of 1 mM to 1.0M, and the mixing takes place at a temperature in the range of 0° C.–60° and a pH in the range of 2–9.

3. The process of claim 1, wherein prior to step e) and subsequent to step d), the biologically active agent-lipid conjugate is contacted with a reducing agent.

4. A process for making a biologically active agent phospholipid conjugate, comprising the steps of:
   a) mixing a reactive phospholipid in an organic solvent with a diketene thereby producing an acetoacetylated phospholipid;
   b) isolating the acetoacetylated phospholipid;
   c) dissolving the acetoacetylated phospholipid in a medium;
   d) mixing the dissolved acetoacetylated phospholipid with a nucleophile containing biologically active agent thereby producing a biologically active agent—phospholipid conjugate; and
   e) isolating the biologically active agent—phospholipid conjugate.

5. The process of claim 4 wherein in step (a), the concentration of the reactive lipid is in the range of 0.001–0.1M, and the mixing takes place at a temperature in the range of 10° C.–50° C. and a pH in the range of 3–8; and in step (d), the concentration of the acetoacetylated lipid is in the range of 1 mM to 1.0M and the mixing takes place at a temperature in the range of 0° C.–60° C. and a pH in the range of 2–9.

6. The process of claim 4, wherein prior to step (e) and subsequent to step (d), the biologically active agent-phospholipid conjugate is contacted with a reducing agent.

7. A process for making a biologically active agent cationic phospholipid conjugate, comprising the steps of:
   a) mixing a reactive cationic phospholipid in an organic solvent with a diketene thereby producing an acetoacetylated cationic phospholipid;
   b) isolating the acetoacetylated cationic phospholipid;
   c) dissolving the acetoacetylated cationic phospholipid in a medium;
   d) mixing the dissolved acetoacetylated cationic phospholipid with a nucleophile—containing biologically active agent thereby producing a biologically active agent—cationic phospholipid conjugate; and
   e) isolating the biologically active agent—cationic phospholipid conjugate.

8. The process of claim 7 wherein in step (a), the concentration of the reactive lipid is in the range of 0.001–0.1M and the mixing takes place at a temperature in the range of 10° C.–50° C. and a pH in the range of 3–8; and in step (d), the concentration of the acetoacetylated lipid is in the range of 1 mM to 1.0M and the mixing takes place at a temperature in the range of 0° C.–60° C. and a pH in the range of 2–9.

9. The process of claim 7 wherein prior to step (e) and subsequent to step (d), the conjugate is contacted with a reducing agent.

* * * * *